United States Patent [19]

Hohmann

[11] 3,989,952
[45] Nov. 2, 1976

[54] DENTAL APPARATUS

[75] Inventor: Eugen Hohmann, Heppenheim, Germany

[73] Assignee: Siemens Aktiengesellschaft, Erlangen, Germany

[22] Filed: Aug. 2, 1974

[21] Appl. No.: 494,273

[30] Foreign Application Priority Data
Aug. 6, 1973 Germany............................ 2339827

[52] U.S. Cl.................................. 307/38; 317/102; 32/22
[51] Int. Cl.².......................................... H02B 1/04
[58] Field of Search....................... 307/38, 11, 24; 317/102; 32/22, 27, DIG. 3

[56] References Cited
UNITED STATES PATENTS

| | | | |
|---|---|---|---|
| 1,462,656 | 7/1923 | Pieper et al............................ | 32/22 |
| 3,058,470 | 10/1962 | Seeliger et al. ...................... | 128/422 |
| 3,544,866 | 12/1970 | McLeroy ............................. | 318/118 |

*Primary Examiner*—Robert K. Schaefer
*Assistant Examiner*—Morris Ginsburg
*Attorney, Agent, or Firm*—Haseltine, Lake & Waters

[57] ABSTRACT

A dental apparatus including a plurality of handpieces, each having associated therewith an electrical appliance such as, for example, a miniature drive motor, a generator for generating HF-oscillations, or an electrical valve for controlling the airflow of a turbine, whose operative condition (rotational speed, power output or valve flow-section) is variable through a change in the operating voltage by means of an adjusting element. The apparatus includes a single electrical supply module for all appliances, which is connected to a voltage source, and whose output provides tap-offs for the appliances, including a common adjusting element for all appliances which is connected in the control circuit of the supply module, through which the output voltage of the supply module may be varied between a minimum and a maximum value, the appliances having switch means associated through which, dependent upon use of one or another handpiece, one or another appliance may be connectable with the output of the supply module, and in which the supply module is so constructed so as to deliver the required operating voltages for obtaining the desired operating condition of the respective appliance.

15 Claims, 7 Drawing Figures

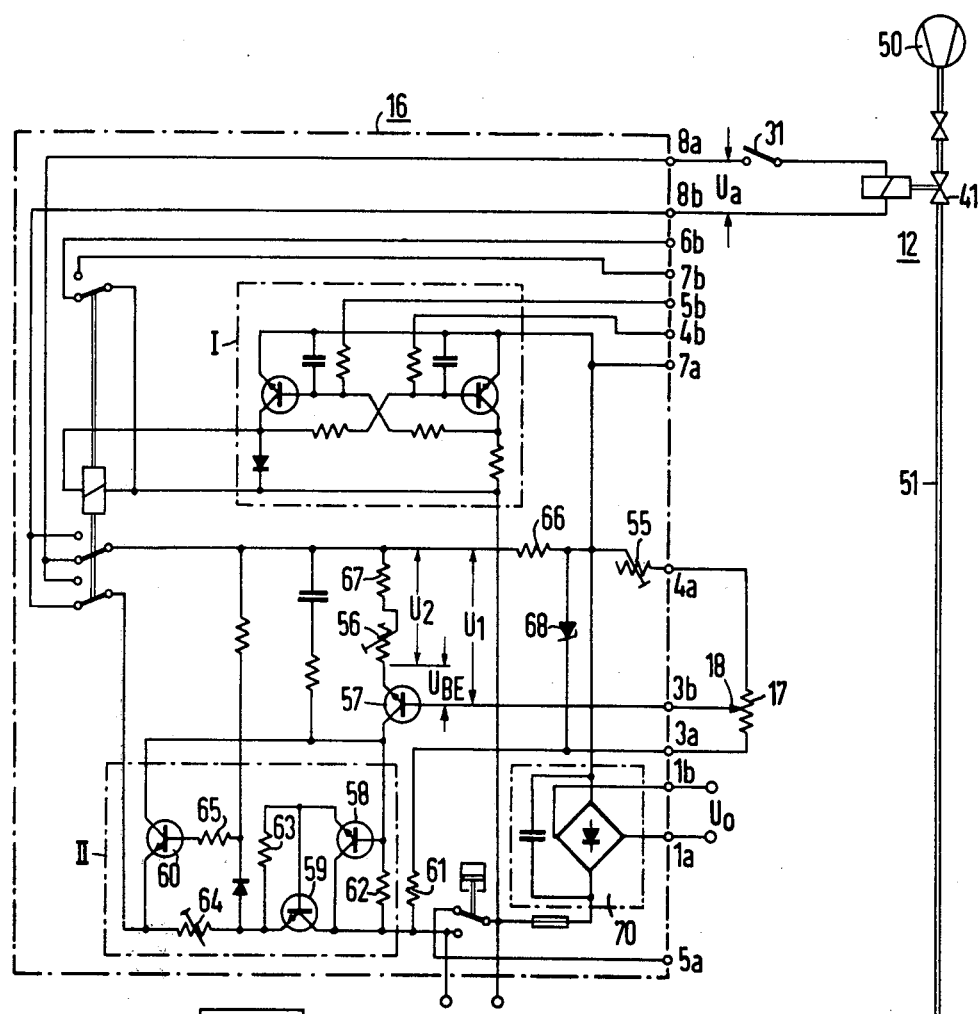
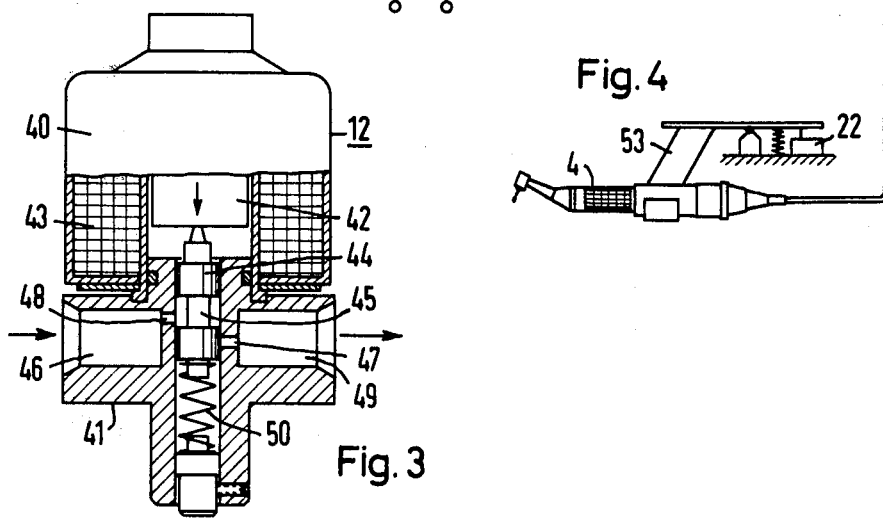
Fig. 4
Fig. 3

DENTAL APPARATUS

FIELD OF THE INVENTION

The present invention relates to a dental apparatus including a plurality of handpieces, each having associated therewith an electrical appliance such as, for example, a miniature drive motor, a generator for generating HF-oscillations, or an electrical valve for controlling the airflow of a turbine, whose operative condition (rotational speed, power output or valve flow-section) is variable through a change in the operating voltage by means of an adjusting element.

DISCUSSION OF THE PRIOR ART

In known apparatus of this type, each handpiece is provided with its own current supply, as well as its own adjustment or, respectively, control arrangement for varying the operative condition of its electrical appliance. The current supply, as well as the control arrangement, are both predetermined on the basis of the electrical appliance for the particular handpiece.

A disadvantage of that type of apparatus lies in that the operating personnel must operate a number of adjusting elements having various types of grips and with different manipulations. Thus, the speed adjustment of the electric motor for a drill handpiece is carried out, for example, by means of a foot control arrangement with a pivotable foot lever; the various current intensities for a pulp testing handpiece or for an electrosurgical handpiece, in contrast therewith, are frequently adjusted by means of a turn knob or slide control which is located in the hand region of the operating personnel. The constant readaptation and rethinking from one to the other adjusting element renders the operation of such an apparatus more difficult. In addition thereto, the range of adjustment of the adjusting element from its zero or initial position to maximum displacement is different for each handpiece. A further disadvantage is that a relatively large space is required for the locations of the particular supply components and adjustment elements.

SUMMARY OF THE INVENTION

Accordingly, it is an object of the present invention to provide a dental apparatus in accordance with the above-described type which, in comparison with such apparatus is, pursuant to the state of the technology, much more simply constructed, and in particular much simpler to operate.

The intended object of the invention is, accordingly, inventively solved in that there is provided for all appliances a single electrical supply module which is connected to a voltage source, whose output provides tap-offs for the appliances, including a common adjusting element for all appliances which is connected in the control circuit of the supply module, through which the output voltage of the supply module may be varied between a minimum and a maximum value, the appliances having switch means associated therewith by means of which, dependent upon use of one or another handpiece, one or another appliance may be connectable with the output of the supply module, and in which the supply module is so constructed so as to deliver the required operating voltages for obtaining the desired operating condition.

In accordance with the invention, one and the same supply module may be employed for a number of handpieces, and namely also for those with different functions in varied constructions. Inasmuch as some of the handpieces are controlled by means of one and the same adjusting element, which preferably is foot operated, the requirements for the control of the individual appliances may be appreciably reduced, and the operation of the apparatus considerably simplified. As an essential advantage it may be ascertained, that the operating personnel can operate each handpiece by means of the same adjusting technique.

Particular advantages are obtained when, in one of the advantageous aspects and further constructions of the invention, the supply module is utilized as a control arrangement serving to provide the rotational speed adjustment of a drill drive motor. That kind of electronic control is, in any event, present in each dental apparatus, inasmuch as a handpiece with an electrical drill drive motor belongs as practically a standard component of a dental apparatus.

As a further important advantage of the invention may be ascertained that the electrical appliances, which are generally known components, do not require any significant modifications with regard to their electrical construction.

BRIEF DESCRIPTION OF THE DRAWINGS

Further advantages may be ascertained from the following detailed description of the invention, taken in conjunction with the accompanying drawings; in which:

FIG. 3 shows an enlarged sectional view of an electromagnetic valve of a turbine handpiece shown in FIG. 2;

FIG. 4 shows a diagrammatic illustration of the supply module for the valve of FIG. 3;

DETAILED DESCRIPTION

Figure 1:
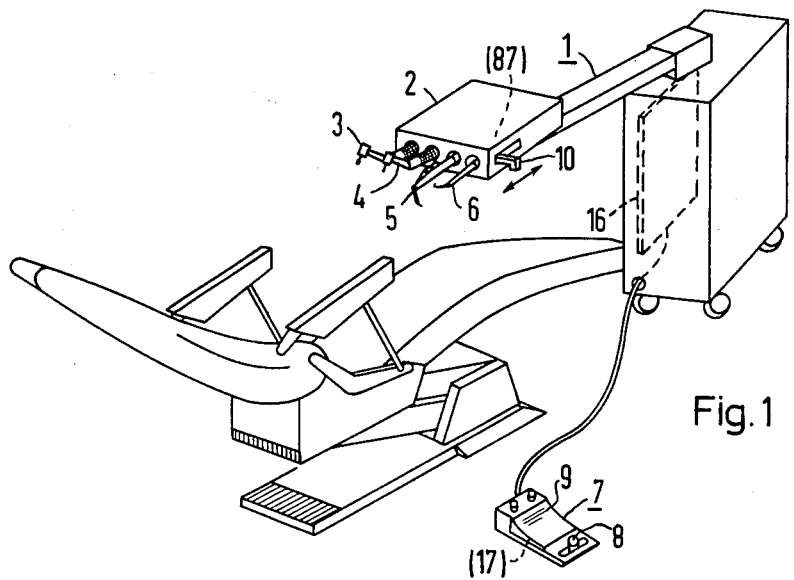
FIG. 1 illustrates, in a perspective view, a dental apparatus according to the present invention.

FIG. 1 illustrates a dental apparatus 1, having associated therewith a patients' chair, which is not further described. The apparatus 1 contains an instrument support table 2 within which are retained handpieces 3 through 6. The handpieces 3 through 6, as viewed in series from left to right, comprise an electric motor handpiece including a miniature motor located in the handpiece, a turbine handpiece, an ultrasonic handpiece for removing tartar, as well as an electro-surgical apparatus for the cutting and electrodesiccating or cauterizing the tooth gum tissue. The apparatus 1 contains a foot control arrangement 7 on which there is located a foot-actuated and horizontally displaceable pivot lever 8, as well as a downwardly actuatable step plate 9. The pivot lever 8 has a definite base or at-rest position and may be pivoted in both directions (left or right) in opposition to a return biasing force. Interiorly of the foot control arrangement, the pivot lever 8 is connected with an intermediate tap-off of a variable resistance 17, whose resistance value is varied in response to the pivoting. The step plate 9 affects a switch (reference numeral 99 in FIG. 5) which, as well as the above-mentioned resistance is constructed as in the hereinbelow described circuit diagram, and whose function is more closely explained therein.

An adjusting element 10 of a slide resistance 87 is located within the instrument support table 2. The function thereof is more closely described in detail in the circuit diagram of FIG. 5. Each handpiece 3 through 6 has an electric appliance associated therewith, whose operative condition may be varied by means of foot control arrangement 7.

Figure 2:
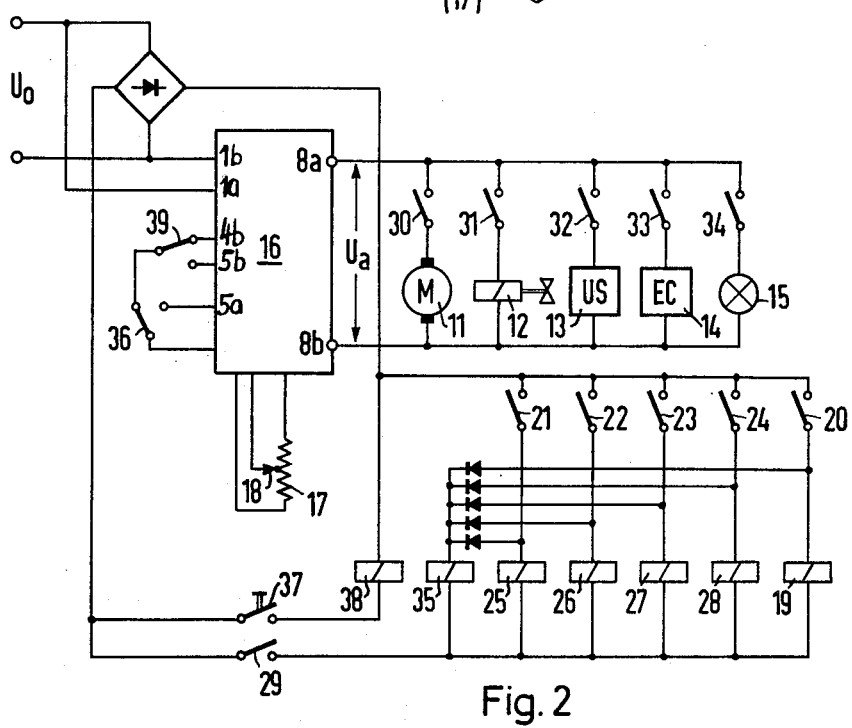
FIG. 2 shows a circuit diagram for the appliances associated with the handpieces in the apparatus of FIG. 1.

FIG. 2 illustrates, through an electrical circuit diagram, the individual appliances for the handpieces 3 through 6. For handpiece 3, the electrical appliance is an electrical miniature motor 11 which is located in the handpiece, for a turbine handpiece 4 the electric appliance is an electromagnetic valve 12 located in apparatus 1, in which the through-flow of compressed air is variable in accordance with a predetermined flow cross-section and by means of which there may be controlled the speed of the turbine located in handpiece 4. At the ultrasonic handpiece 5 there is provided a generator 13 for producing ultrasonic vibrations. By varying the voltage of the generator 13, the ultrasonic output may be varied within a predetermined range. In the electro-surgical handpiece 6, the electric appliance is a generator 14 for producing high-frequency or HF-oscillations. The circuit arrangement of both generators 13 and 14 is hereinbelow not further detailed, since they relate to generally known circuits. Thus, a generator for producing ultrasonic vibrations is described, for example, in U.S. Pat. No. 3,544,866; and a generator for producing high-frequency oscillations for example, in U.S. Pat. No. 3,058,470. Finally, reference numeral 15 designates an electric light of an examining light, which is not illustrated in FIG. 1, and which may also be formed as a handpiece.

The electrical appliances 11 through 15 are supplied from a single supply module 16, which is powered by a supply voltage source $U_O$ (generally 110 or, respectively, 220 volts), with a low voltage in the range of 0 to 24 volts. The variable resistance is designated by reference numeral 17, through which, by changing the tap-off 18 (connected with the pivot lever 8), the output voltage $U_a$ at the contacts 8a, 8b of the supply module 16 may be continually varied within the range of 0 to 24 volts. For correspondingly switched-in appliances (11 through 15), the particular operative condition thereof (rotational speed of motor 11, flow-through cross-section of valve 12 and consequent rotational speed of the turbine in handpiece 4, power output of the ultrasonics and, respectively, high-frequency energy of the generators 13 and 14, as well as the light intensity of lamp 15) may be continually varied.

The electrical appliances 11 through 15 are switched in by means of switches 20 through 24, which are actuated by withdrawal of the corresponding handpiece 3 through 6, and the respectively unillustrated eventually additional lamp handpiece. The switches 20 through 24 may, in accordance with the illustration of FIG. 4, be connected in such a manner with correspondingly constructed support arrangements for the handpieces, so that upon withdrawal of a handpiece from its support arrangement, the therewith associated switch (20 to 24) is closed. Thus, by means of relays 19 and 25 through 28, upon actuation of the in-and-out switch 29, the latter of which is connected with the pivot lever 8 of the foot control arrangement 7, the associated relay contacts 30 through 34 are actuated. Through the intermediary of coupling diodes, a further relay 35 is concurrently excited, whose contact 36 imparts a voltage to the supply module 16. A control key is designated by reference numeral 37, whose actuation activates a relay 38 having a reverse switching contact 39 by means of which the rotational direction of motor 11 is reversed by reversing the polarities of the connecting contacts. Details which are not inventive need no further be discussed herein. The key 37 suitably is located within the instrument support table 2, or in the foot control arrangement 7. From the circuit diagram there may be ascertained that all five appliances are adapted to be connected to the same output 8a, 8b. In correspondence with the position of the pivot lever 8, and therewith the slide 18 on the resistance 17, the output voltage $U_a$ is regulatable from 0 to about 24 volts. If the voltage ranges, within which the particular operative condition of appliances 11 through 15 are to be varied, are in conformance with the voltage range 0 to 24 volts for the supply module 16, then no further measures must be met. If these, however, deviate from the maximum or, respectively, minimum value of the output voltage of the supply module then the circuit must be modified, as described in connection with the exemplary embodiment pursuant to FIG. 5.

FIG. 3 illustrates, partially in section, the construction of the electromagnetic valve 12 for the turbine handpiece 4. The valve 12 essentially consists of two components, a lifting magnet 40 and a throttle valve 41. A magnetic armature or plunger 42 is provided within the lifting magnet 40 which, upon excitation of the magnetic winding 43, is axially displaced within complementary shaped guide (as shown by the arrow). The magnetic armature 42 displaces a piston 44, which is axially movable within the valve body 41, and which is provided with a recess 45 extending along the axial length thereof. In a predetermined position, the recess 45 connects an air inlet passageway 46 through two apertures 47 and 48 with an outlet passageway 49. The pressurized air flows, after passage through the valve, toward the turbine which is located in the handpiece 4. The higher the voltage at the lifting magnet 40, then the greater is the movement of piston 44 in the direction of the arrow, and the larger is the open flow-through cross-section between the apertures 47 and 48. A spring 50, which tends to move the piston 44 in opposition to the force of the magnet is so dimensioned as to render possible a linear displacement of the piston 44.

FIG. 4 illustrates the construction of the supply module 16, as an example, in connection with the thereto connected control valve 12 for the turbine handpiece 4. The valve 12 is supplied with pressurized air which is transmitted from a compressed air generator 50 through a compressed air conduit 51 to the turbine located in handpiece 4. The support arrangement 53 for the handpiece 4 consists of a support cradle which, upon removal of the handpiece 4, actuates the switch 22 (FIG. 2). This provides for preselection of the valve 12. Upon displacement of pivot lever 8 (FIG. 1) from its middle or central position, the resistance value at the potentiometer 17 is varied, which results in a change in the output voltage at the terminals 8a, 8b of the supply module 16. At a closed contact 31, the voltage at valve 12 and consequently the flow of air through valve body 41 may be changed so as to lead to a change in the rotational speed of the turbine which is located in handpiece 4.

The supply module 16 provides a circuit arrangement which may be employed for the control of the speed of an electrical drill drive motor 11. Such a circuit arrangement must in general fulfill a number of requirements, namely, to undertake a stable speed variation of the motor, to maintain the speed of the motor constant independently of the load acting on the drill tool and additionally to also limit the current flow, and finally to permit a change in the rotational direction of the motor. Since for variation of the operative conditions at the other appliances 12 through 15 there are important only the means which are required for a rotational adjustment of a motor, in the following portion of the description consideration is primarily given to this portion of the circuit arrangement.

For the rotational speed adjustment of the miniature electro-motor 11 essentially of importance is the controllable resistance 17 (adjusting resistance) with its variable tap-off 18, the resistance 55 for limiting the upper rotational speed, the resistance 56 for limiting the lower rotational speed, the transistors 57 through 60, as well as the resistances 61 through 67, diodes and the direct-voltage supply 70. The resistance 66 is a load dependent operative resistance which lies in the armature current circuit of the drive motor 11. At the transistor 59 which, as a variable resistance is similarly located at the motor armature circuit and which with a collector-emitter-section lies in series with the resistance 66, there is applied a voltage $U_T$ 59. The transistor 58 is controlled at its base by the collector potential of the transistor 57. At the base-emitter-section of the transistor 57 there is applied a control voltage $U_{BE} = U_1 + R_{66}$. The bias voltage $U_1$ is thereby taken from a voltage divider formed from resistance 17 and resistance 55 whose voltage is maintained constant through the intermediary of diode 68, independently of the magnitude of the applied direct-voltage from the supply source 70. The smaller becomes the voltage $U_1$ through the potentiometer 17, the smaller becomes the base-emitter voltage $U_{BE}$ of the transistor 57, which closes for so much more; its collector potential thereby becoming more positive. This has the result that the transistors 58 and 59 are more largely opened. Thereby, the voltage at the collector-emitter-section of the transistor 57 reduces. This again provides the result that the output voltage $U_1$ at the terminals 8a, 8b correspondingly increases, so that there is applied a higher voltage at the appliance, valve 21. The flow through aperture in the valve body 51 thereby becomes correspondingly larger, so as to lead to a higher air flow and thereby to an increase in the rotational speed of the turbine in the handpiece 4.

Through variation of the resistance value of the potentiometer 17, at the terminals 8a, 8b of the supply module 16 in accordance with the thereto connected electrical appliance, there may be selectively changed the rotational speed of the electro-motor 11, the rotational speed of the turbine 12, the intensity of lamp 15, the oscillating amplitude of the ultrasonic generator 13, or the frequency of the electro-surgical apparatus 14.

Figure 5:
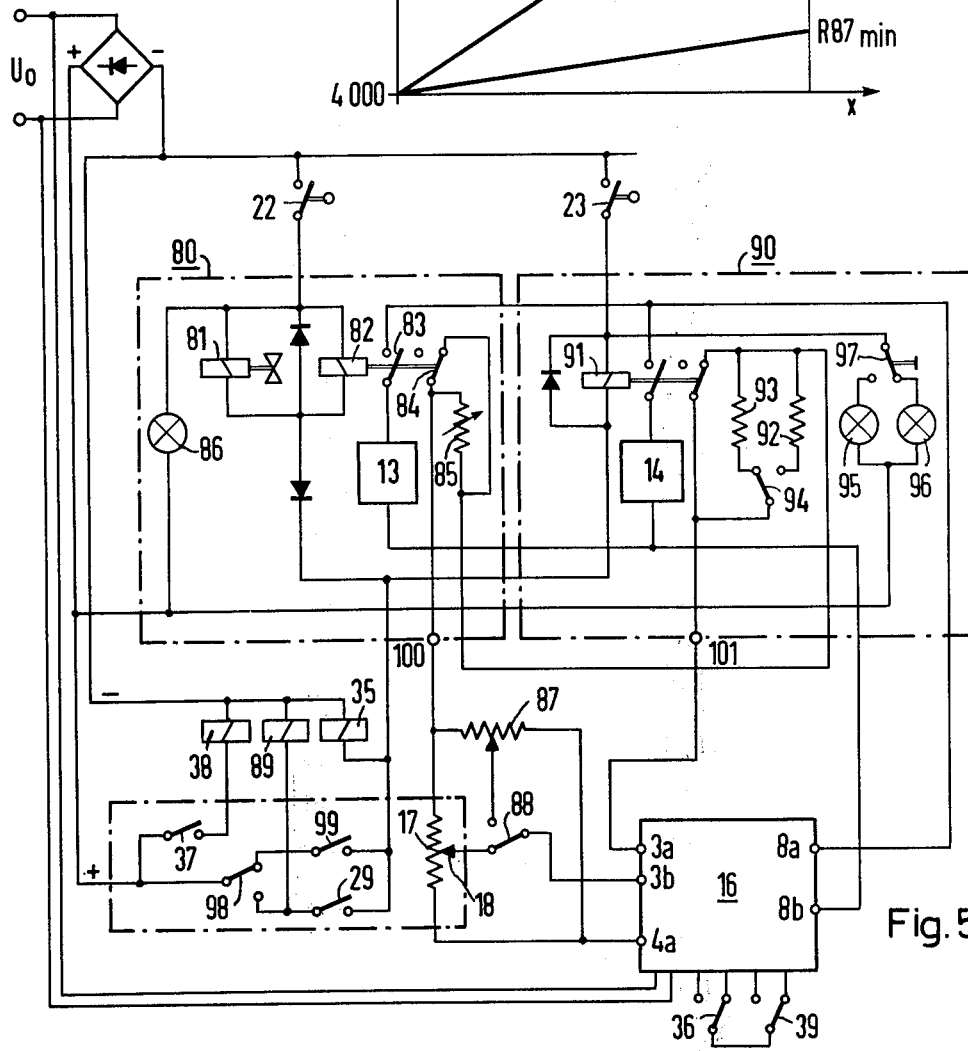
FIG. 5 shows a circuit diagram for the control of the inventive apparatus.

If for attaining the desired operative conditions, the required voltages at the individual appliances do not coincide with the attainable voltages at the terminals 8a, 8b (in this case 0 to 24 volts), of the common supply module, which frequently is the case since ultrasonic apparatus in general are regulated between 18 through 24 volts, electro-surgical apparatus for cutting between 15 to 24 volts and for cauterizing or fulgurating between 9 through 24 volts, and the flow-through valve between 7 and 24 volts, then the circuit construction must be provided, as shown in FIG. 5. The circuit construction is explained, for example, with respect to the generators 13 and 14 of an ultrasonic component 80 and an electro surgical component 90. The ultrasonic component 80 includes a water magnetic valve 81, a relay 82 with contacts 83 and 84, the generator 13 for producing the ultrasonic vibrations, and a regulatable resistance 85, as well as a control lamp 86.

If the ultrasonic handpiece 5 (FIG. 1) is removed from its support in the instrument table 2, then the conduit switch 22 closes immediately. The signal lamp 86 illuminates and indicates that the ultrasonic component 80 is in its prepared condition. Within the foot control arrangement 7 (FIG. 1) there are located the switches 29, 37, 99, as well as potentiometer 17, which are shown in the lower left-hand portion of FIG. 5 encompassed by a chain-dotted line. Through switch 98, the control circuit for the components may be conducted either through switch 29 which is connected with the pivot lever 8 (FIG. 1) and which is switched on upon displacement of the lever from a definite basic position, or through the switch 99 which is connected with the switch plate 9 and which is actuated upon stepping on the latter.

The switch 37 serves the purpose, upon connection of motor 11, to change the rotational direction thereof. This may be carried out by means of relay 38 and its associated contact 39. By means of relay 89 there is actuated the reversing switch 88. The relay 35 switches switch 36.

If the switch 29 is actuated (displacement of pivot lever 8 from its at-rest position) then, provided the handpiece has been previously removed from its support and consequently the conduit switch 22 is closed, the water magnetic valve 81 and relay 82 are excited. By means of contacts 83, 84 of relay 82, on the one hand, the ultrasonic generator 13 is connected with the output of the electronic control 16 and, on the other hand, connected through the stationary contact 84, a resistance 85 is connected in series with the adjusting resistance 17. Positioned in parallel with resistance 17 is a further resistance 87, which advantageously is located within the instrument support table 2, and which may be adjusted by means of adjusting element 10 (FIG. 1). The resistance 87 suitably is formed as a slide resistance and has no definite at-rest position, in effect meaning, that the adjusting element remains stationary in each set position and does not automatically return into its initial position, as is the case with resistance 17. With the connection of resistance 85 to the adjusting resistance 17 there is achieved that the voltage range of normally about 0 or respectively 3.5 to 24 volts, which is required for the operation of motor 11 (FIG. 2), is limited to approximately 18 to 24 volts. This restriction of the voltage range is required inasmuch as ultrasonic generator 13 at voltages below 18 volts only supplies a very low ultrasonic energy to the respective tool in the handpiece 5. The minimum output of the generator 13 thus is given at 18 volts, and the maximum output at 24 volts. Upon a not depressed switch 29 and open conduit switch 24 (handpiece 5 having been returned to its support position), the resistance 85 is bridged, the electronic control 16 in this switch position provides an output voltage of 0 or respectively 3.5 to 24 volts which, as previously mentioned, is required for the operation of the miniature motor 11. Through the switching-in of the resistance 85 in series with the adjusting resistance 17, the output voltage at terminals 8a, 8b is restricted to within the range of 18 to 24 volts, without thereby varying the pivotal angle (displacement extent) of the pivot lever 8. This is an important advantage of the inventive object. The physician thus may, with the same adjusting element and with the same extent of movement, change the operative condition of a number of appliances which must be regulated within varied voltage ranges.

The electro-surgical component 90 operates in accordance with the same principle. Also in this instance, for an excited switch relay 91, a resistance 92 or 93 is connected in series with adjusting resistance 17. Since the electro-surgical component 90 fulfills two functions, namely cutting and fulgurating or cauterizing, two different resistances 92 and 93 are required which are respectively switched-in by means of a switch 94 into the control cicuit 3a, 3b, 4a of the component. Through reference numerals 95, 96 are designated two indicator lamps which indicate the operatively prepared condition of the selected function (cutting or fulgurating). The switch 97 suitably is connected with the reversing switch 94. The generator 14, similar to the generator 13, includes a practically sufficiently known circuit arrangement, which need not be further detailed within the framework of the present disclosure.

The arrangement of resistance 87, which lies in parallel with the adjusting resistance 17 in the hand manipulative range of the operator, is amongst other things thus so advantageous inasmuch as the apparatus 1 may be selectively operated thereby through a foot control arrangement with an on-off circut, in which the particular appliance may be switched in-and-out by foot, and a control in the hand manipulative range of the operator (for example, by means of slide regulator 10) can be carried out (Alternative A), or through a foot control arrangement with regulating characteristics (Alternative B) as illustrated in FIG. 1 (reference numeral 7). In a foot control arrangement with an on-off circuit (Alternative A) the rotational speed may be adjusted by means of a potentiometer 87 which is located in the hand manipulative region (actuated through the slide regulator 10). In accordance with the circuit arrangement of FIG. 5, without the necessity of significant circuit-wise changes, there may be employed one or the other of the other control alternatives. The switch 98 is connected with a suitable locking arrangement (not shown). In the operation of the handpiece pursuant to the on-off circuit, the switch 98 not only switches the control circuit over from one switching mode (switch 99) to the other (switch 29), but concurrently herewith relay 89 is excited, whose reverse switch contact 88 connects the center tap-offs of both parallel-connected resistances 17 and 87 of the control circuit with the connector 37 of the supply module 16.

Figure 7:
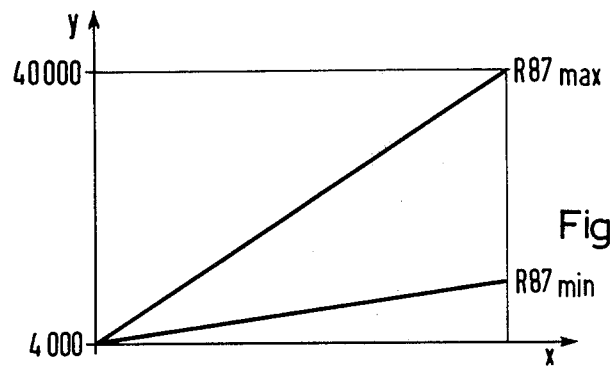
FIG. 7 is a graphical representation of the operating characteristics of the inventive apparatus.
Figure 6:
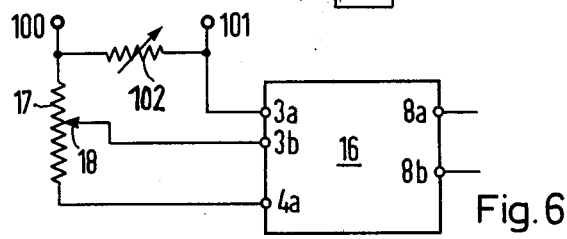
FIG. 6 shows a fragmentary view of a modified circuit.

FIG. 6 illustrates another alternate solution for the operation of the apparatus in accordance with Alternative A, as well as B. In contrast with the circuit arrangement shown in FIG. 5, in this instance, there is provided in the control circuit 3a, 4a of the supply module 16, a resistance 102 which is connected in series with the adjusting resistance 17. The resistance 102 has a resistive value which is at least 10 times the resistive value of the adjusting resistance 17. In conformance with the circuit construction of FIG. 5, to the connections 100 and, respectively, 101 there may be connected the components 80 and respectively 90. The illustrated arrangement affords the following advantages:

During operation with control characteristic (Alternative B), in accordance with the graphical diagram of FIG. 7, there may be preselected the maximum rotational speed or also the maximum output by means of a preselective potentiometer 102. In the graphical diagram along the ordinate there is indicated the rotational speed, and along the abscissa the displacement of pivot lever 8 (FIG. 1). The parameter is the setting of the preselective potentiometer. In the case of motor rotational speed control, there is attained herein a spread in the lower rotational speed range, facilitating a fine sensitive regulation through the potentiometer 17 which located in the foot manipulative region. The preselection of the maximum rotational speed through the potentiometer 102 has, in addition thereto, the further advantage that is meaningful in particular for users in operative locations who are in training, that the maximum rotational speed may be individually limited by the training supervisor.

During the use of the foot control arrangement pursuant to Alternative A, independently of the potentiometer setting of the potentiometer 17, the rotational speed may be continually and gradually adjusted between a minimum and a maximum value through regulatable resistance 102. This is in particular obtained, in that the preselective potentiometer has at least a 10 times larger resistive value then the potentiometer 17 which is located in the foot control arrangement 7.

While there has been shown what is considered to be the preferred embodiment of the invention, it will be obvious that modifications may be made which come within the scope of the disclosure of the specification.

What is claimed is:

1. In a dental apparatus including a plurality of handpieces; an electrical appliance operatively associated with respectively each said handpiece; and adjusting means for varying the operating voltage supplied to each said appliance so as to change the operative condition thereof, the improvement comprising: a single electrical supply module including a control circuit, said module having an input connected to a voltage supply source and an output connectable to said electrical appliances, said adjusting means including a single foot-controllable adjusting element positioned in the control circuit of said electrical supply module for varying the output voltage of said module between a minimum and a maximum value; switch means connected to each said electrical appliance which, in dependence upon the use of a particular handpiece, selectively connect a respective one of said appliances with the output of said electrical supply module; and means in said electrical supply module for delivering a required operating voltage to the respective switched-in appliance so as to impart the desired operative condition to said appliance.

2. A dental apparatus as claimed in claim 1, said electrical appliances being respectively constituted of an electrical miniature drive motor, a generator for producing HF-oscillations, and an electrical valve for controlling the air flow through a turbine, said adjusting means being adapted to change the rotational speed, output, and valve flow-through section of respectively said appliances.

3. A dental apparatus as claimed in claim 1, said electrical appliances having an operating voltage variable between a maximum and a minimum value deviating from the maximum to minimum output voltage of said electrical supply module, comprising means connectable into said control circuit for correlating the available output voltage of said module with the required voltage of a respective switched-in appliance.

4. A dental apparatus as claimed in claim 3, said adjusting means comprising a first variable resistace located in a foot-controllable proximity to a user of said apparatus, said switched-in appliance including a second resistance connected in series with said variable resistance, said second resistance having a resistive value measured to so as to correlate the maximum and, respectively, minimum voltage at the output of said electrical supply module with the voltage range of said appliance.

5. A dental apparatus as claimed in claim 4, said second resistance being connected into said control circuit of said module upon actuation of said appliance.

6. A dental apparatus as claimed in claim 4, comprising support means for each said handpiece, switch means adapted to be actuated in response to removal of a handpiece from its respective support means; and relays controlled by said switch means, said relays including switch contacts for connecting the appliance of the respective handpiece with the output of said electrical supply module and the second resistance in series with said first variable resistance.

7. A dental apparatus as claimed in claim 4, comprising a third variable resistance in hand-controllable proximity to said user being connected in parallel to said first variable resistance; and reversing switch means for selectively connecting said first and third variable resistances into the control circuit of said electrical supply module.

8. A dental apparatus as claimed in claim 4, comprising a third variable resistance in hand-controllable proximity to said user, said third variable resistance being connected in series with said first variable resistance and in parallel to said second resistance.

9. A dental apparatus as claimed in claim 8, the resistive value of said third variable resistance being a multiple of the resistive value of said first variable resistance.

10. A dental apparatus as claimed in claim 9, said third variable resistance having 10 times the resistive value of said first variable resistance.

11. A dental apparatus as claimed in claim 7, comprising adjusting means for said third variable resistance, said foot-controllable adjusting element for said first variable resistance having a predefined base position, said adjusting means for said third variable resistance not having a defined base position.

12. A dental apparatus as claimed in claim 8, comprising adjusting means for said third variable resistance, said foot-controllable adjusting element for said first variable resistance having a predefined base position, said adjusting means for said third variable resistance not having a defined base position.

13. A dental apparatus as claimed in claim 11, comprising a housing encompassing said first variable resistance and said adjusting element, said adjusting element including a pivot lever projecting from said housing; first and second switch means in said housing for actuation of said appliances, said first switch means being actuated upon displacement of said pivot lever from its base position; and step plate means on said housing; said second switch means adapted to be actuated upon depression of said step plate means.

14. A dental apparatus as claimed in claim 13, comprising a reversing switch for selectively connecting said first and second switch means into actuating current circuit of said appliances, said reversing switch including means for detachably arresting said pivot lever in an operative end position.

15. A dental apparatus as claimed in claim 1, said electrical supply module comprising a circuit arrangement for effecting rotational speed changes of a drill drive motor, said circuit arrangement including an operative resistance located in the base current circuit of said drive motor, a power transistor having the collector-emitted-section thereof connected in series with said operative resistance, and a voltage divider connected in parallel to the series circuit of the collector-emitter-section of said power transistor and the motor armature, and connected in series with said operative resistance so as to influence the base potential of said power transistor through its tap-off.

* * * * *